United States Patent [19]

Broom

[11] 4,282,236
[45] Aug. 4, 1981

[54] β-LACTAM ANTIBACTERIAL AGENTS, THEIR USE IN PHARMACEUTICAL COMPOSITIONS, AND INTERMEDIATES

[75] Inventor: Nigel J. P. Broom, Dorking, England

[73] Assignee: Beecham Group Limited, England

[21] Appl. No.: 92,179

[22] Filed: Nov. 7, 1979

[51] Int. Cl.³ .............................. C07D 499/00
[52] U.S. Cl. ................. 424/270; 260/245.2 R
[58] Field of Search .............. 424/270; 260/245.2

[56] References Cited

U.S. PATENT DOCUMENTS

| 4,153,714 | 5/1979 | Ponsford | 260/245.2 |
| 4,155,912 | 5/1979 | Menard | 260/306.7 C |
| 4,168,314 | 9/1979 | Christensen et al. | 260/245.2 |
| 4,182,711 | 1/1980 | Ueda | 548/178 |
| 4,215,124 | 7/1980 | Christensen et al. | 424/270 |

FOREIGN PATENT DOCUMENTS

| 2210 | 6/1978 | European Pat. Off. |
| 3415 | 8/1979 | European Pat. Off. |
| 10358 | 4/1980 | European Pat. Off. |
| 866845 | 11/1978 | France |
| 2005246 | 4/1979 | United Kingdom |
| 2014574 | 8/1979 | United Kingdom |

Primary Examiner—Nicholas S. Rizzo
Attorney, Agent, or Firm—Jacobs & Jacobs

[57] ABSTRACT

The compounds of the formula (II):

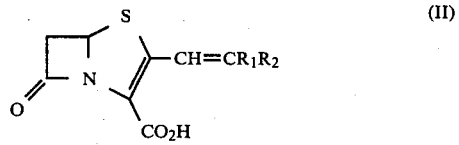

and salts and cleavable esters thereof wherein $R_1$ is a hydrogen atom or a lower alkyl group and $R_2$ is a CN or $CO_2R_3$ group where $R_3$ is a hydrogen atom or a lower alkyl, aryl, or aralkyl group are antibacterially effective compounds. Their preparation and use is described.

12 Claims, No Drawings

β-LACTAM ANTIBACTERIAL AGENTS, THEIR USE IN PHARMACEUTICAL COMPOSITIONS, AND INTERMEDIATES

R. B. Woodward (Acta Pharm. Suecica 1977, 14 Suppl., p 23-25) disclosed that the compounds of the formula (I):

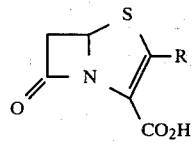

where R was an unspecified group possessed antibacterial activity. No aid in determining the nature of the group R was given by Professor Woodward nor did he describe the preparation of any compounds of the formula (I). However, at the symposium on Current Topics in Drug Research (Uppsala, Sweden October 1977) Professor Woodward described the compound of the formula (I) wherein R is a hydrogen atom. We have prepared this compound and found it to possess a somewhat disappointing degree of antibactrial activity. Clearly it would be desirable to find a class of compound that possess a better degree of activity especially against Gram-positive organisms such as *Staphylococcus aureus, Streptococcus pneumoniae* or *Streptococcus pyogenes*. Such a class of compounds has now been found.

Accordingly the present invention provides the compounds of the formula (II):

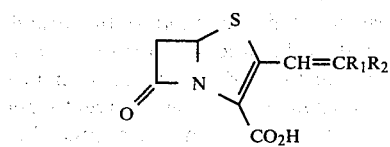

and salts and cleavable esters thereof wherein $R_1$ is a hydrogen or atom or a lower alkyl group and $R_2$ is a CN or $CO_2R_3$ group where $R_3$ is a hydrogen atom or a lower alkyl, aryl, or aralkyl group.

When used herein the term "lower alkyl" means an alkyl group of 1-4 carbon atoms such as the methyl and ethyl groups. When used herein the term "aryl" means a phenyl group or a phenyl group substituted by a halogen atom or an alkoxyl group of 1 or 2 carbon atoms. When used herein the term "lower aralkyl" means a lower alkyl group substituted by an aryl group.

Most suitably $R_1$ is a hydrogen atom.

Suitable values for $R_2$ include the cyano, methoxycarbonyl, ethoxycarbonyl and benzyloxycarbonyl groups.

It is believed that the compounds of the formula (II) or their salts are the antibacterially active species and that biologically cleavable esters thereof act as pro-drugs. Thus in one favoured aspect this invention provides the compounds of the formula (II) wherein $R_1$ is as hereinbefore defined and pharmaceutically acceptable salts therof. Non-pharmaceutically acceptable salts of the compounds of the formula (II) also form part of this invention since they may be used as chemical intermediates, for example in the preparation of pharmaceutically acceptable salts by ion-exchange. Thus suitable salts of the compounds of the formula (II) include the lithium, sodium, potassium, calcium and magnesium salts and salts of nitrogenous bases. Particularly suitable salts of this invention include the sodium and potssium salts. Alternatively active esters of the compounds of the formula (II) are believed to be those cleavable by in-vivo hydrolysis to the compounds of the formula (II) or their salt. Such esters may be identified by administration to a test animal such as a rat or a mouse by intravenous administration and thereafter examining the test animals body fluids for the presence of the compound of the formula (II) or its salt.

Suitable esters of this type include those of the part formulae (a) and (b):

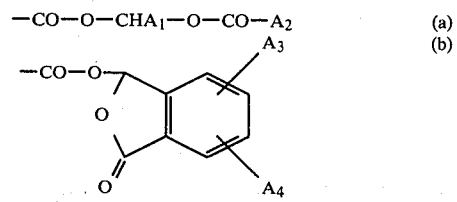

where $A_1$ is a hydrogen atom or a methyl group, $A_2$ is an alkyl or alkoxyl group of 1-4 carbon atoms or a phenyl group, $A_3$ is a hydrogen atom or a methyl or methoxyl group and $A_4$ is a hydrogen atom or a methyl or methoxyl group. Other esters of the compounds of the formula (II) of interest are those cleavable by chemical methods as described hereinafter.

The present invention also provides a pharmaceutical composition which comprises a compound of the formula (II) or a pharmaceutically acceptable salt or in-vivo hydrolysable ester thereof and a pharmaceutically acceptable carrier.

Most suitably the composition of this invention comprises a compound of the formula (II) or a pharmaceutically acceptable salt thereof. It is particularly suitable that the compositions of this invention comprises a sodium or potassium salt of a compound of the formula (II).

The compositions of this invention may be in a form suitable for injection or for oral administration such as tablets or capsules. In general such compositions are in unit dose form and contain from 50 mg to 1000 mg and more usually from 100 mg to 500 mg. Such compositions may be administered once or more times per day so that the daily dose for a 70 kg adult is in the range 500 mg to 2500 mg.

The compositions of this invention may be formulated in the manner of known antibiotics such as ampicillin. Thus for example an injectable solution may be prepared by dissolving 100 mgs of a sodium salt of a compound of the formula (II), for example that where $R^1$ is a methyl group, in sterile water for injection BP. Alternatively, such a compound may be formulated into a tablet or capsule in standard manner with such excipients as lubricant, disintegrant, filler, binder or the like, for example magnesium stearate, microcrystalline cellulose, sodium starch glycollate, polyvinylpyrrolidone, polyvinylpolypyrrolidone or the like.

The compositions of this invention may also comprise a penicillin or cephalosporin if desired. Amoxycillin, for example as the trihydrate or sodium salt, is particularly apt for use in such mixed compositions.

The present invention also provides a process for the preparation of a compound of the formula (II) or a salt or cleavable ester thereof which process comprises the oxidation of a cleavable ester of the compound of the formula (III):

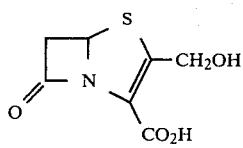

(III)

to yield a cleavable ester of the compound of the formula (IV):

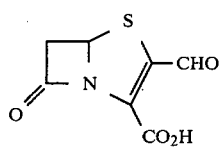

(IV)

and thereafter reacting with a Wittig reagent of the formula (V):

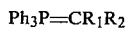

Ph₃P=CR₁R₂    (V)

wherein R₁ and R₂ are defined as in relation to formula (II) and thereafter if desired cleaving the ester to yield the compound of the formula (II) or its salt.

Suitable cleavable ester groups include those removable by hydrogenolysis and those removable by hydrolysis. Esters conventionally removable by hydrogenolysis include substituted benzyl esters, such as the nitrobenzyl esters of which the p-nitrobenzyl ester is preferred. Such esters may be cleaved by hydrogenation, for example using palladium on charcoal as catalyst.

Particularly suitable esters for removable by hydrolysis include silyl esters such as the trimethylsilyl, tert-butyldiphenyl silyl and the like esters. The tertbutyldiphenylsilyl ester is particularly apt as it is readily cleavable by treatment with fluoride ion.

The oxidizing agent used for oxidizing the ester compound of the formula (II) is most suitably manganese dioxide. The oxidation is normally effected in an aprotic medium such as dichloromethane at an non-extreme temperature such as 0° to 30°, for example at ambient temperature. It is frequently convenient to use this solution in which the ester of the compound of the formula (IV) is prepared in the subsequent Wittig reaction.

The Wittig reaction is normally effected in an aprotic medium such as dichloromethane at a non-extreme temperature such as 0° to 30°, for example at ambient temperature. The cleavable ester of the compound of the formula (II) may be isolated by evaporation of the solvent followed if desired by chromatographic purification, for example over silica gel eluting with ethyl acetate/petroleum mixtures. Recrystallisation from ethyl acetate/petroleum mixtures may be used to further improve the purity of the product.

In a further aspect this invention provides a process for the preparation of a compound of the formula (II) or a salt thereof which comprises the hydrogenation of the p-nitrobenzyl ester of the compound of the formula (II) optionally in the presence of base.

The hydrogenation reaction may employ an approximately atmospheric pressure of hydrogen using a palladium catalyst such as palladium on charcoal, for example 5% palladium on charcoal. Conventional hydrogenation solvents may be used such as dioxane and water, for example a 4:1 mixture.

The initially produced compound of the formula (II) may be neutralised by reaction with a base which may be present during the hydrogenation or introduced thereafter. Suitable bases include LiCO₃, LiOH, Na₂CO₃, NaHCO₃, KHCO₃, Ca(OH)₂, MgO or the like.

The desired salt may be obtained by diluting with a water immiscible solvent and extracting the salt into water. Evaporation of the aqueous solution yields the desired salt. Purification may be effected chromatographically.

Cleavable esters of the compounds of the formula (II) may be prepared by conventional methods of esterifying salts of carboxylic acids. Thus, for example a sodium salt of a compound of the formula (II) may be reacted with a reactive chloride or bromide in dimethylformamide or like solvent.

The processes of this invention generally lead to the preparation of compounds racemic at C-5. It is believed that the more active isomer is that of the formula (VI):

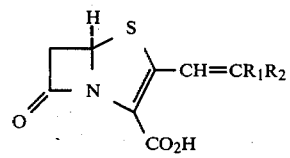

(VI)

and salts and cleavable esters thereof wherein R₁ and R₂ are as defined in relation to formula (II).

The cleavable esters of the compounds of the formula (III) may be prepared by the process of the other application made this day in the U.K. in the name of Beecham Group Limited naming N. Broom as inventor and entitled "Bicyclic β-lactam antibacterial agents, their use in pharmaceutical compositions, processes for their preparation and intermediates for use in such processes". and incorporated herein by reference. The necessary reaction sequence may be set forth thus:

HO₂C . CH₂ . OH ⟶ HO₂C . CH₂ . OSiʳBDP ⟶

HS . CO . CH₂ . OSiʳBDP

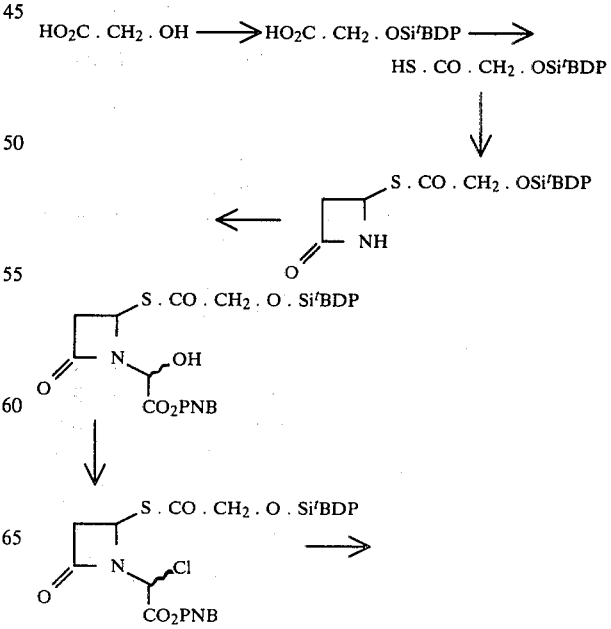

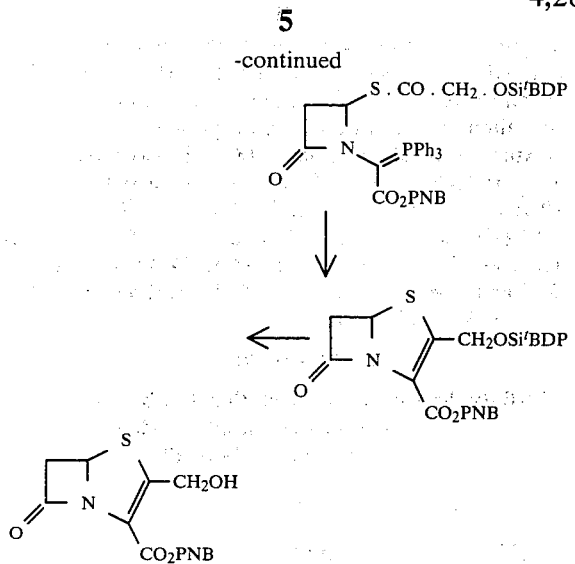

In the preceeding Scheme Si'BDP means tert-butyl-diphenylsilyl and PNB means p-nitrobenzyl.

In the following illustrative Examples and Descriptions all column chromatography was carried out using Merck Silica gel 60 (7729). Petroleum ether means petroleum ether b.p. 60°-80°. PNB means p-nitrobenzyl.

DESCRIPTION 1

Benzyl O-t-butyldiphenylsilyl-glycollate (2)

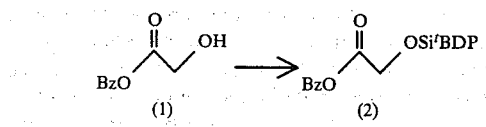

To a stirred solution of benzyl glycollate (1) (4.15 g, 25 mmol) (J. C. Michaeu and A. Latles, Bull. Soc. Chim. Fr., 1970, 4018) and imidazole (3.74 g, 55 mmol) in dry DMF (200 mls) under argon was added a solution of t-butyldiphenylsilyl chloride (7.55 g, 27.5 mmol) in DMF (20 ml). After 1 hour the reaction mixture was poured into ethyl acetate (1,000 mls), washed well with water, dried ($Na_2SO_4$) and evaporated to give a yellow oil. Chromatography of the crude reaction mixture on silica gel eluting with ethyl acetate/petroleum* mixtures gave the ester (2) (7.4 g, 73%) as an oil. $\nu_{max}$. ($CHCl_3$) 1750 $cm^{-1}$. δ ppm ($CDCl_3$) 1.10 (9H, s), 4.30 (2H, s); 5.15 (2H, s); 7.13–7.90 (15H, m).

*Denotes petroleum ether b.p. 60°-80° throughout this document. Also Bz denotes the benzyl group, Si'BDP denotes the t-butyldiphenylsilyl group, DMF denotes dimethylformamide and DCM denotes dichloromethane. PNB denotes the p-nitrobenzyl group.

DESCRIPTION 2

O-t-Butyldiphenylsilyl-glycollic acid (3)

Method A

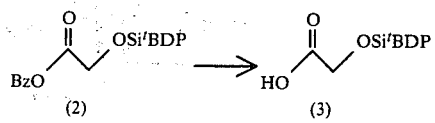

The ester (2) (4.04 g, 10 mmol) in ethanol (100 ml) was hydrogenated over 10% palladium on charcoal catalyst (0.5 g) at N.T.P. until the theoretical amount of hydrogen had been consumed. The mixture was filtered through Kieselguhr and the residue washed with ethanol. The combined filtrates were evaporated to give the acid (3) (3 g). δ ppm ($CDCl_3$), 1.10 (9H, s), 4.30 (2H, s), 7.20–7.95 (10H, m), 9.00 (1H, bs, exch. $D_2O$).

Method B

A solution of glycollic acid (2.28 g, 30 mmol) in DMF (300 ml) was sequentially treated with imidazole (5.10 g, 75 mmol) and t-butyldiphenylsilyl chloride (9.87 g, 36 mmol). After half an hour the reaction mixture was poured into ethyl acetate (1.5 liter), washed well with 5 N HCl, dried ($Na_2SO_4$) and evaporated to give the acid (3) 8.40 g). The material was essentially the same as that prepared in Example 2, and was of sufficient purity for further synthetic work.

DESCRIPTION 3

O-t-Butyldiphenyl silyl-thioglycollic acid (4)

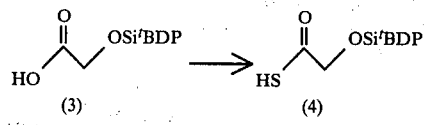

A solution of the acid (3) (2.22 g) and triethylamine (1 ml) in dry dichloromethane (50 ml) was stirred at room temperature for ten minutes. The solution was then cooled to −15° and ethyl chloroformate (0.7 ml) was added. After a further twenty minutes, more triethylamine (1 ml) was added and hydrogen sulphide was passed into the reaction mixture. After thirty minutes the mixture was warmed to room temperature, solvent was removed and toluene (50 ml) added. The mixture was filtered and the filtrate evaporated to give the triethylamine salt of the thioacid (4). This was redissolved in ether (50 ml), washed with 5 N HCl, dried ($Na_2SO_4$) and evaporated to give the thioacid (4) (2.1 g) as an oil. $\nu_{max}$. ($CHCl_3$) 2560, 1690 $cm^{-1}$. δ ppm ($CDCl_3$) 1.15 (9H, s) 4.20 (2H, s), 4.92 (1H, bs, exch. $D_2O$), 7.25–8.00 (10H, m).

DESCRIPTION 4

4-t-Butyldiphenylsilyloxyacetothio-azetidin-2-one (6)

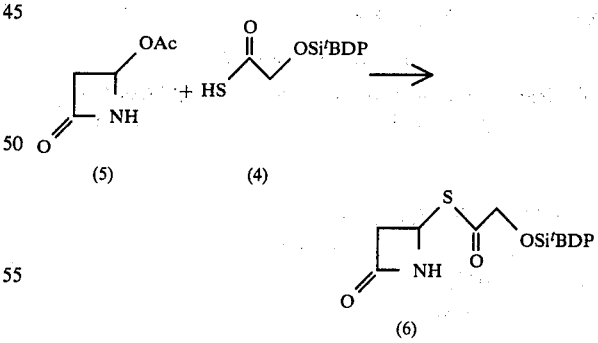

To a solution of sodium hydroxide (0.28 g) in water (30 ml) at 5° was added the thioacid (4) (2.1 g), followed after ten minutes by 4-acetoxyazetidin-2-one (5) (0.9 g) in dichloromethane (30 ml). The two-phase mixture was vigorously stirred and warmed to room temperature over one hour. Dilute citric acid solution (10 ml) was added and the organic phase separated. The aqueous phase was further extracted with dichloromethane (3×15 ml). The combined organic phase was dried ($Na_2SO_4$), evaporated and chromatographed on silica gel eluting with ethyl acetate/petroleum mixtures gave the azetidinone (6) (1.15 g) as a colourless gum which slowly solidified, m.p. 57°–9° (plates from ethyl acetate/petroleum); $\nu_{max}$. (EtOH) 222 nm Em 17,500), $\nu_{max}$. (CHCl$_3$) 3420, 1770, 1690 cm$^{-1}$, δ ppm (CDCl$_3$) 1.12 (9H, s), 3.00 (1H, ddd, J=1, 2.5, 15 Hz, which collapses to 1H, dd, J=2.5, 15 Hz on D$_2$O exh.), 3.46 (1H, ddd, J=1.5, 5, 15 Hz, collapses to 1H, dd, J=5, 15 Hz on D$_2$O exch.), 4.22 (2H, s), 5.16 (1H, dd, J=2.5, 5 Hz), 6.40 (1H, bs, exch. D$_2$O), 7.24–7.80 (10H, m). (Found: C, 63.22; H, 6.39; N, 3.27; S, 7.99%. C$_{21}$H$_{25}$NO$_3$SSi requires C, 63.12; H, 6.31; N, 3.51; S, 8.02%.

DESCRIPTION 5

4-t-Butyldiphenylsilyloxyacetothic-1-(1-hydroxy-1-benzyloxycarbonylmethyl)-azetidin-2-one (7)

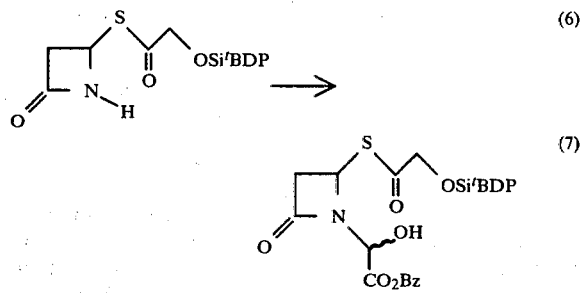

A solution of the azetidinone (6) (1.1 g, 2.76 mmol) and benzyl glyoxylate (0.94 g, 5.94 mmol) in benzene (70 ml) was refluxed with provision for azotropic removal of water for eighteen hours. The reaction mixture was washed with water, dried (Na$_2$SO$_4$), evaporated and chromatographed on silica eluting with ethyl acetate/petroleum mixtures. This gave the hydroxy ester (7) (1.35 g) (87%) as a 1:1 mixture of epimers. $\nu_{max}$. (CHCl$_3$) 3600–3200, 1760, 1690 cm$^{-1}$. δ ppm (CDCl$_3$) 1.11 (9H, s), 3.02 and 3.09 (1H, dd, J=3, 15 Hz, trans-C3-H epimers), 3.40 and 3.47 (1H, dd, J=5, 15 Hz, cis-C3-H epimers), 3.89 and 4.27 (1H, d, J=8 Hz, each. D$_2$O, —OH epimers), 4.22 (2H, s), 5.04 and 5.29 (centers of ABq, J=12 Hz) and 5.27 (s), (2H, —CO$_2$CH$_2$Ph epimers), 5.40 and 5.50 (1H, dd, J=3, 5 Hz, C4-H epimers), 5.47 (1H, d, J=8 Hz, collapses to 1H, s, on D$_2$O exch.) 7.30–7.50 (15H, m).

DESCRIPTION 6

4-t-Butyldiphenylsiloxyacetothio-1-(1-chloro-1-benzyl oxycarbonyl methyl)-azetidin-2-one (8)

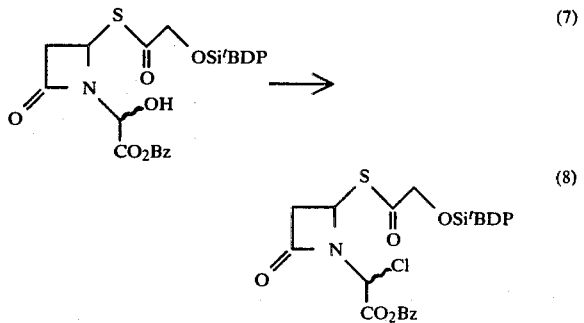

A stirred solution of the hydroxy esters (7) (1.13 g, 2 mmol) in THF (50 ml) at −10° was sequentially treated with lutidine (0.35 ml, 3 mmol) and thionyl chloride (0.22 ml, 3 mmol). A white precipitate immediately formed. After twenty minutes the reaction mixture was filtered and the solid washed with THF (10 ml). The filtrate was evaporated, redissolved in toluene (50 ml) and filtered. The fitrate was evaporated to give a 1:1 mixture of the chloro epimers (8) (1.2 g) as a yellow oil. $\nu_{max}$. (CHCl$_3$) 1780, 1700 cm$^{-1}$. δ ppm (CDCl$_3$) 1.11 (9H, s), 3.10 and 3.14 (1H, dd, J=25, 16 Hz), 3.61 and 3.63 (1H, dd, J=5, 15 Hz), 4.22 (2H, s), 5.10 and 5.24 (centres of ABq, J=12 Hz) and 5.27 (s) (2H, in total), 5.61 and 5.64 (1H, dd, J=2.5, 5 Hz) 6.02 and 6.07 (1H, s), 7.18–7.71 (15H, m).

DESCRIPTION 7

4-t-Butyldiphenylsilyoxyacetothio-1-[1-benzyloxycarbonyl-1-triphenyl phosphorylidene methyl]-azetidin-2-one (9)

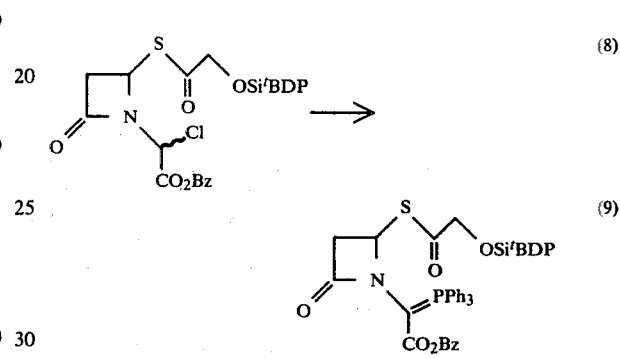

A solution of chloro ester epimers (8) (1.16 g, 2 mmol), lutidine (0.28 ml, 2.4 mmol) and triphenyl phosphine (1.05 g, 4 mmol) in dry dioxane (40 ml) was stirred under argon at 50° for eighteen hours. The reaction mixture was filtered and the solid washed with dioxane (10 ml). The filtrate was evaporated, dissolved in ethyl acetate (50 ml), washed with 2 N HCl, brine, dried (Na$_2$SO$_4$) and evaporated. Chromatography on silica gel eluting with ethyl acetate/petroleum mixtures gave the phosphorane (9) (0.73 g, 45%) as a colourless oil which foamed $\nu_{max}$. (CHCl$_3$) 1740, 1690, 1680, 1610 cm$^{-1}$. (Found: C, 71.22; H, 5.54; N, 1.77; S, 3.82%. C$_{48}$H$_{46}$NO$_5$PSSi requires C, 71.35; H, 5.74; N, 1.73; S, 3.97%).

DESCRIPTION 8

Benzyl 2-(t-Butyldiphenylsiloxymethyl) penem-3-carboxylate (10)

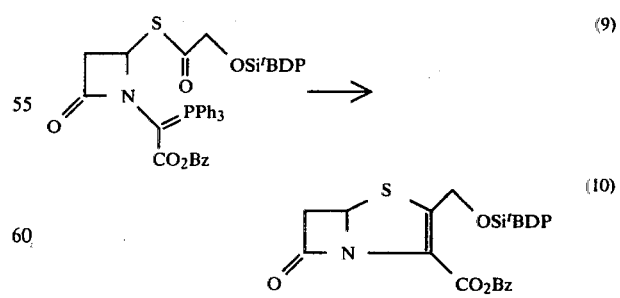

A solution of phosphorane (9) (528 mg, 0.65 mmol) was refluxed in dry toluene (300 ml) under argon for 2½ hours. The solvent was removed and the mixture chromatographed on silica gel eluting with ethyl acetate/petroleum mixtures to give the penem (10) (230 mg, 68%)

as a gum that slowly solidified, m.p. 89°–90° (needles from ethyl acetate/petroleum). $\nu_{max}$. (EtOH) 265 (Em 2,360), 323 (8,050) nm. $\nu_{max}$. (CHCl$_3$) 1785, 1700, 1580 cm$^{-1}$. δ ppm (CDCl$_3$), 1.04 (9H, s), 3.44 (1H, dd, J=2, 16 Hz), 3.78, 5.56 (1H, dd, J=2, 4 Hz), 7.20–7.78 (15H, m). (Found: C, 67.83; H, 5.90; N, 2.87; S, 6.10%. C$_{30}$H$_{31}$NO$_4$SSi requires, C, 68.02; H, 5.90; N, 2.64; S, 6.05%).

DESCRIPTION 9

Benzyl-2-Hydroxymethyl penem-3-carboxylate (11)

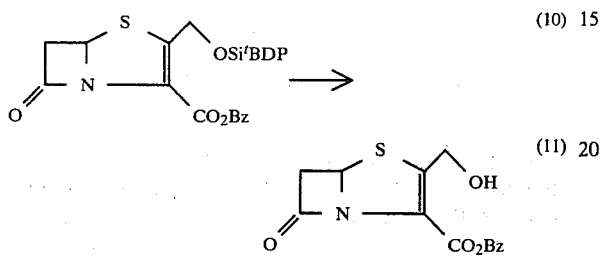

A solution of the penem (10) (18 mg) and tetraethylammonium fluoride (containing 20–25% water) (20 mg) in THF (5 ml) was stirred at room temperature for two hours. Ethyl acetate (15 ml) was added and the mixture washed well with water, dried (Na$_2$SO$_4$) and evaporated. Chromatography on silica gel eluting with ethyl acetate/petroleum mixtures afforded the 2-hydroxymethyl penem benzyl ester (11). $\nu_{max}$. (CHCl$_3$) 3600–3000, 1790, 1700, 1575 cm$^{-1}$.

DESCRIPTION 10

4-t-Butyldiphenylsiloxyacetothio-1-(1-p-nitrobenzyloxycarbonyl-1-hydroxymethyl)-azetidin-2-one (12)

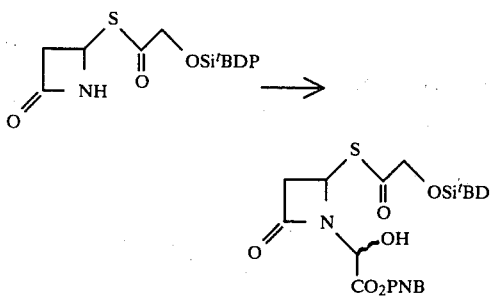

A solution of the azetidinone (6) (4.00 g, 10 mmol) and p-nitrobenzyl glyoxylate (4.54 g, 20 mmol) in benzene (150 ml) was refluxed with provision for azeotropic removal of water for eighteen hours. The reaction mixture was washed with water, dried (Na$_2$SO$_4$) and evaporated. Chromatography on silica gel eluting with ethyl acetate/petroleum mixtures gave an epimeric mixture of the hydroxy-esters (12) (4.65 g, 76%) as a foam. $\nu_{max}$. (CHCl$_3$) 3600–3200, 1775, 1695, 1520, 1350 cm$^{-1}$. δ ppm (CDCl$_3$) 1.18 (9H, s), 2.90–3.30 (1H, m), 3.30–3.68) (1H, m), 3.50–4.20 (1H, bs, exch. D$_2$O), 4.25 (2H, s), 5.20–5.65 (4H, m), 7.20–7.80 (12H, m), 8.05–8.33 (2H, m).

DESCRIPTION 11

4-t-Butyldiphenylsilyoxyacetothio-1-(1-p-nitrobenzyloxycarbonyl-1-chloromethyl)-azetidin-2-one (13)

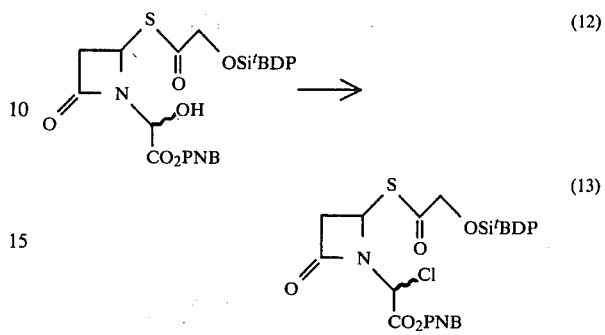

A stirred solution of the hydroxy esters (12) (3.5 g, 5.76 mmol) in THF (200 ml) at −10° under argon was sequentially treated with lutidine (1.04 ml, 8.63 mmol) and thionyl chloride (0.63 ml, 8.63 mmol). A white precipitate immediately formed. After twenty minutes the reaction mixture was filtered and the solid washed with THF (50 ml). The filtrate was evaporated, redissolved in toluene (200 ml) and filtered. The filtrate was again evaporated to give the chloro esters (13) (3.6 g) as a yellow gum. $\nu_{max}$. (CHCl$_3$) 1775, 1695, 1520, 1350 cm$^{-1}$. δ ppm (CDCl$_3$) (3:2 epimer ratio; a:b) 1.20 (9H, s), 3.11$^a$ and 3.16$^b$ (1H, dd, J=4, 16 Hz); 3.60$^b$ and 3.64$^a$ (1H, dd, J=6, 16 Hz), 4.22 (2H, s), 5.23$^a$ and 5.36$^b$ (2H, bs), 5.56–5.73 (1H, m), 6.06$^a$ and b.10$^b$ (1H, s), 7.33–7.64 (12H, m), 8.09–8.27 (2H, m).

DESCRIPTION 12

4-t-Butyldiphenylsilyoxyacetothio-1-(1-p-nitrobenzyloxycarbonyl-1-triphenylphosphorylidenemethyl)-azetidin-2-one (14)

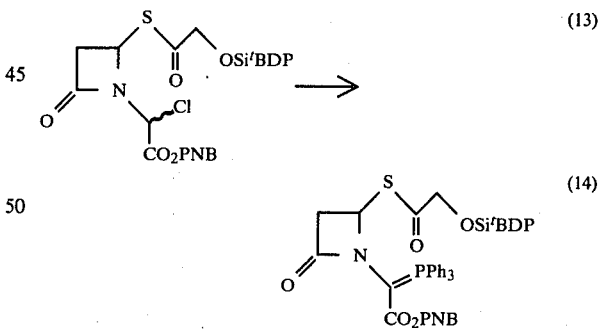

A solution of the chloro ester epimers (13) (3.6 g, 5.75 mmol), lutidine (0.83 ml, 6.9 mmol) and triphenyl phosphine (3.02 g, 11.5 mmol) in dry dioxane (150 ml) were stirred under argon at 45° for eighteen hours. The reaction mixture was filtered and the solid washed with dioxane (50 ml). The filtrate was evaporated, dissolved in ethyl acetate (200 ml), washed with 2 N HCL and brine. The dried organic phase was evaporated and chromatographed on silica gel eluting with ethyl acetate/petroleum mixtures to give the phosphorane (14) (3.5 g, 71%) as a yellow foam. $\nu_{max}$. (CHCl$_3$) 1740, 1690–1680, 1615, 1515, 1345 cm$^{-1}$.

DESCRIPTION 13

4-t-Butyldiphenylsilyoxyacetothio-1-(1-p-nitrobenzyloxycarbonyl-1-triphenylphosphorylidenemethyl)-azetidin-2-one Trifluoracetic acid salt (15)

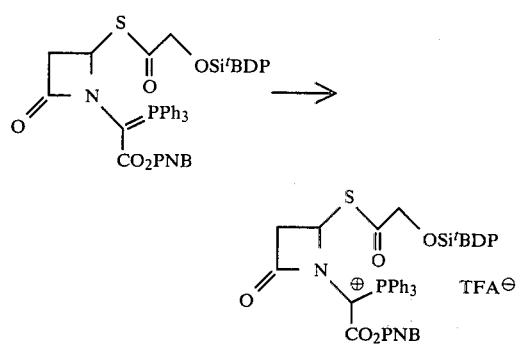

To a stirred solution of the phosphorane (14) (3.6 g, 4.22 mmol) in ethyl acetate (250 ml) was added trifluoroacetic acid (17 mls, 4 eq.). After fifteen minutes, the solvent was removed, toluene (250 ml) was added, and the solvent re-evaporated. This process was repeated four times to give the phosphonium salt (15) (4.35 g) as a light yellow foam. $\nu_{max}$ (CHCl$_3$) 1750, 1170 cm$^{-1}$.

DESCRIPTION 14

4-Hydroxyacetothio-1-(1-p-nitrobenzyoxycarbonyl-1-triphenylphosphorylidinemethyl)-azetidin-2-one (16)

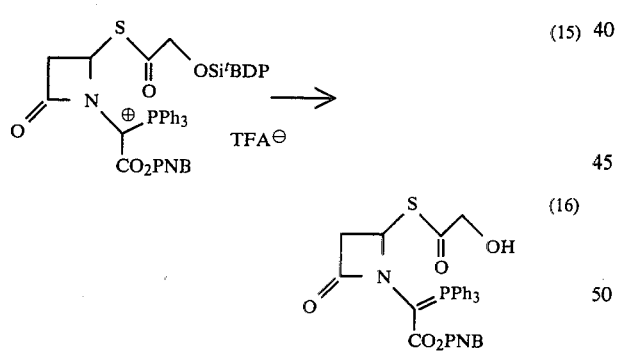

A stirred solution of the phosphonium salt (15) (2.9 g, 3 mmol) in THF (150 ml) under argon was treated with a solution of tetrabutylammonium fluoride (9 mmol) in THF. After half an hour the mixture was evaporated, redissolved in ethyl acetate (200 ml) and washed with saturated sodium bicarbonate solution (3×100 ml), water (50 ml) and brine (100 ml). The dried organic phase was evaporated and chromatographed on silica gel eluting with ethyl acetate/petroleum mixtures to give the phosphorane (16) (1.3 g). $\nu_{max}$ (CHCl$_3$) 3600–3000, 1750, 1685, 1620 cm$^{-1}$.

DESCRIPTION 15 p-Nitrobenzyl 2-Hydroxymethylpenem-3-carboxylate (17)

Method A

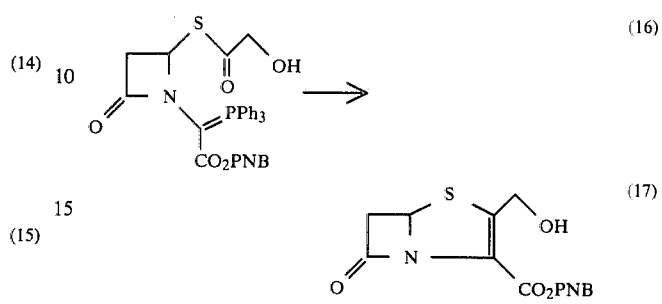

A solution of the phosphorane (16) (1.3 g) in purified toluene (700 ml) was stirred at 100° under argon. After one and three-quarter hours the solvent was removed and the residue chromatographed on silica gel eluting with ethyl acetate/petroleum mixtures to give the penem (17) (0.34 g) as a yellow solid. m.p. 137°–9° (needles from ethyl acetate/petroleum, $\nu_{max}$ (EtOH), 265 (12,510), 322 (10,450). $\nu_{max}$ (CHCl$_3$) 3600–3010, 1795, 1705, 1580 cm$^{-1}$. δ ppm (CDCl$_3$) 3.11–3.40 (1H, bs. exch. D$_2$O), 3.51 (1H, dd, J=2, 16 Hz), 3.84 (1H, dd, J=4, 16 Hz), 4.67 (2H, bs, collapses to s on D$_2$O exch.), 5.22 and 5.47 (2H, centres of ABq, J=14 Hz) 5.67 (1H, dd, J=2, 4 Hz), 7.60 (2H, d, J=8 Hz), 8.20 (2H, d, J=8 Hz). (Found: C, 50.21; H, 3.43; N, 8.26; S, 9.52%. C$_{14}$H$_{12}$N$_2$O$_6$S requires C, 50.00; H, 3.60; N, 8.33; S, 9.53%).

DESCRIPTION 16 p-Nitrobenzyl 2-(t-Butyldiphenylsilyloxymethyl)penem-3-carboxylate (18)

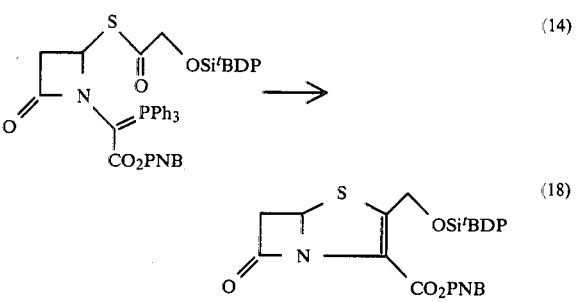

A solution of the phosphorane (14) (400 mg) in dry toluene (300 ml) was refluxed under argon for two hours. The solvent was removed and the mixture chromatographed on silica gel:eluting with ethyl acetate/petroleum mixtures afforded the penem (18) (160 mgs, 60%) as an amorphous solid, 5 m.p. 103°–4° (needles from ether/petroleum). $\nu_{max}$ (EtOH) 268 (13,660), 324 (10,300), $\nu_{max}$ 1785, 1700, 1575 cm$^{-1}$. δ ppm (CDCl$_3$) 1.07 (9H, 2) 3.50 (1H, dd, J=2, 16 Hz), 3.83 (1H, dd, J=4, 16 Hz), 4.86 (2H, s), 5.08 and 5.29 (2H, centres of ABq, J=14 Hz), 5.62 (1H, dd, J=2 4 Hz), 7.25–7.75 (12H, m) 8.11 (2H, d, J=8 Hz). (Found: C, 62.72; H, 5.35; N, 48.2; S, 5.36%. C$_{30}$H$_{30}$N$_2$O$_6$SSi requires: C, 62.69; H, 5.26; N, 4.87; S, 5.58%.

DESCRIPTION 17 p-Nitrobenzyl 2-Hydroxymethylpenem-3-carboxylate (17)

(Method B)

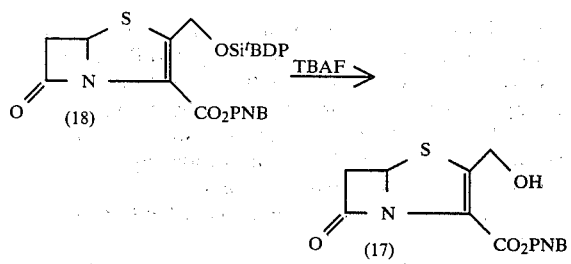

A solution of penem (18) (100 mgs, 0.18 mmol) in THF (20 ml) under argon at −15° was treated with a solution of tetrabutylammonium fluoride (0.27 mmol) in THF. After half an hour the mixture was poured into ethyl acetate (50 ml) and washed with water (5×30 ml). The dried organic phase was evaporated and chromatographed on silica gel eluting with ethyl acetate/petroleum mixtures to give the penem (17) (14 mg). Material identical (i.r. and n.m.r. spectra) with that obtained via Method A.

DESCRIPTION 18

Sodium 2-Hydroxymethyl penem-3-carboxylate (19)

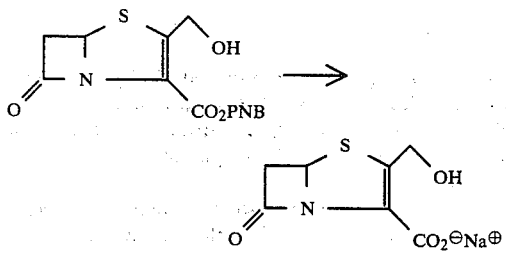

The penem ester (17) (60 mg) was dissolved in a mixture of dioxane (6 ml) and water (1.5 ml) and hydrogenated over 5% palladium on charcoal catalyst (90 mg) for one hour. A further amount of catalyst (60 mg) was added and the hydrogenation continued for a further two hours. A 1% solution of sodium bicarbonate (1.35 ml) was added and the mixture filtered through Kieselguhr. The mixture was evaporated to low volume, water (15 ml) was added and the aqueous solution washed with a little ethyl acetate. Evaporation of the aqueous phase afforded the sodium salt (19) (30 mg) as an amorphous solid. $\lambda_{max}$. (EtOH). 301 nm.

EXAMPLE 1 p-Nitrobenzyl 2-Formyl penem-3-carboxylate (20)

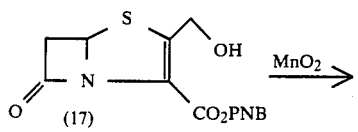

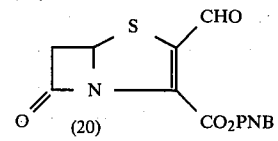

A mixture of the alcohol (17) (100 mg) and activated manganese dioxide (400 mg) in dry dichloromethane (5 ml) were stirred at room temperature for one hour. The mixture was filtered to afford a yellow solution of the aldehyde (20). $\lambda_{max}$. (CH$_2$Cl$_2$) 1805, 1720, 1670, 1610, 1560 cm$^{-1}$. The aldehyde (20) was routinely kept in solution in dichloromethane and was of sufficient purity for further synthetic work.

EXAMPLE 2 p-Nitrobenzyl 2-(trans-2-Carbomethoxy-vinyl) penem-3-carboxylate (21)

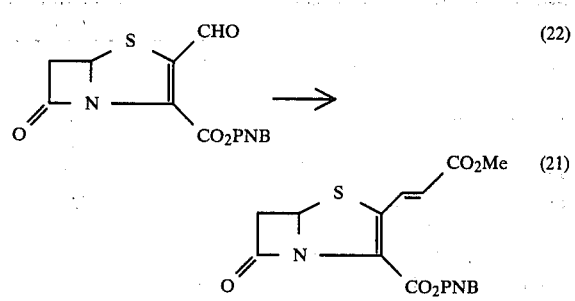

A solution of the aldehyde (20) (prepared from (17) (100 mg) as in Example (1) in dichloromethane (15 ml) was treated with a solution of carbomethoxymethylenetriphenylphosphorane (100 mg) in dichloromethane (5 ml). After five minutes the solution was evaporated and chromatographed on silica gel eluting with ethyl acetate/petroleum mixtures to give the diene (21) (40 mg) as a yellow amorphous solid, m.p. 157°-8° (orange rosettes from ethyl acetate/petroleum). $\nu_{max}$. (EtOH) 264 (7,000), 378 (3,600) n.m. $\nu_{max}$.(CHCl$_3$), 1800, 1720, 1610 cm$^{-1}$. δ ppm (CDCl$_3$) 3.57 (1H, dd, J=2, 16 Hz), 3.78 (4H, bs), 5.27 and 5.49 (2H, centres of ABq, J=12 Hz), 5.69 (1H, dd, J=2, 4 Hz), 6.13 (1H, d, J=16 Hz), 7.63 (2H, d, J=8 Hz), 8.18 (2H, d, J=8 Hz), 8.34 (1H, J=16 Hz). (Found: C, 52.26; H, 3.68; N, 7.01; S, 8.25%. C$_{17}$H$_{14}$N$_2$O$_7$S requires C, 52.30; H, 3.61; N, 7.18, S, 8.21%).

EXAMPLE 3

Sodium 2-(trans-2-Carbomethoxy-vinyl) penem-3-carboxylate (22)

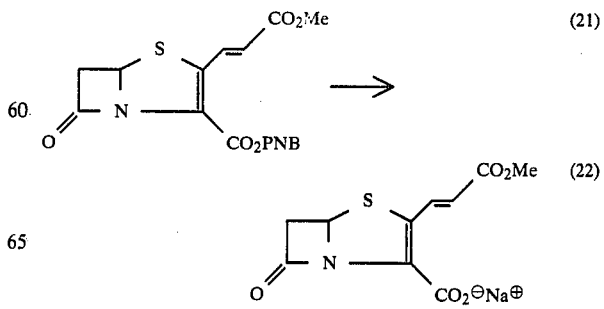

The penem ester (21) (30 mg) was dissolved in a mixture of dioxane (4 ml) and water (1 ml) and hydrogenated over 5% palladium on charcoal catalyst (45 mg) for one hour. A further amount of catalyst (30 mg) was added and the hydrogenation was continued for a further one and a half hours. A 1% solution of sodium bicarbonate (0.6 ml) was added and the mixture filtered through Kieselguhr. The mixture was evaporated to low volume, water (10 ml) was added, and the aqueous solution washed with a little ethyl acetate. Evaporation of the aqueous phase afforded the sodium salt (22) (17 mg) as an amorphous solid. $\lambda_{max}$. (EtOH) 364 n.m. The minimum inhibitory concentrations (MIC) of this compound required to inhibit the growth of various bacteria are tabulated below.

| Organism | Agar[1] | Broth[2] |
|---|---|---|
| Citrobacter freundii E8 | 25 | |
| Enterobacter cloacae N1 | 50 | |
| Escherichia coli 0111 | 25 | 62 |
| Escherichia coli JT 39 | 100 | 250 |
| Klebsiella aerogenes A | 25 | 31 |
| Proteus mirabilis C977 | 25 | 125 |
| Proteus morganii I580 | 50 | |
| Proteus rettgeri WM16 | 50 | |
| Proteus vulgaris W091 | 50 | |
| Pseudomonas aeruginosa A | >100 | >500 |
| Salmonella typhimurium CT10 | 50 | 125 |
| Serratia marcescens US20 | 50 | |
| Shigella sonnei MB 11967 | 100 | |
| Bacillus subtilis A | 5.0 | |
| Staphylococcus aureus Oxford | 5.0 | 8.0 |
| Staphylococcus aureus Russell | 10 | 16 |
| Staphylococcus aureus 1517 | 50 | |
| Streptococcus faecalis I | — | |
| Streptococcus pneumoniae CN33 | 0.5 | |
| Streptococcus pyogenes CN10 | 2.5 | |
| E. coli ESS | 25 | |

1. DST agar + 10% horse blood
2. Microtitre using nutrient broth

{ inoculum 0.001 ml of a $10^{-2}$ dilution for G÷ve bacteria or a $10^{-4}$ dilution for G—ve organisms Minimum Inhibitory Concentrations are expressed in microgrammes per ml.

What I claim is:
1. A compound of the formula (II):

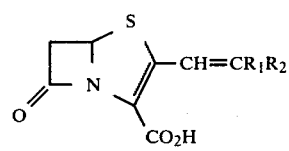

or a salt or cleavable ester thereof wherein $R_1$ is a hydrogen atom or a lower alkyl group and $R_2$ is a CN or $CO_2R_3$ group where $R_3$ is hydrogen or lower alkyl, or phenyl unsubstituted or substituted by halogen or alkoxyl of one or two carbon atoms or lower alkyl substituted by phenyl or phenyl substituted by halogen or alkoxy of one or two carbon atoms.

2. A compound as claimed in claim 1 wherein $R_1$ is a hydrogen atom.

3. A compound as claimed in claim 1 wherein $R_2$ is a CN, methoxycarbonyl, ethoxycarbonyl or benzyloxycarbonyl group.

4. A pharmaceutically acceptable salt of a compound of the formula (II) as claimed in claim 1.

5. A sodium or potassium salt of a compound of claim 1.

6. An ester of a compound of the formula (II) as claimed in claim 1 wherein the ester moiety is of the sub-formula (a) or (b):

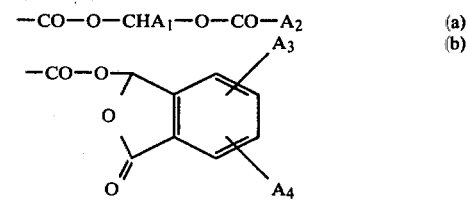

wherein $A_1$ is a hydrogen atom or a methyl group, $A_2$ is an alkyl or alkoxy group of 1–4 carbon atoms or a phenyl group, $A_3$ is a hydrogen atom or a methyl or methoxy group and $A_4$ is a hydrogen atom or a methyl or methoxyl group.

7. A pharmaceutical composition which comprises a carrier and an anti-bacterially effective amount of a compound of the formula (II) as claimed in claim 1 or a salt or ester thereof.

8. A cleavable ester of 2-formylpenem-3-carboxylate.

9. p-Nitrobenzyl 2-formylpenem-3-carboxylate.

10. p-Nitrobenzyl 2-(trans-2-carboxymethylvinyl)-penem-3-carboxylate.

11. A pharmaceutically acceptable salt of 2-(trans-2-carbomethoxyvinyl)penem-3-carboxylic acid.

12. The compound of claim 1 which is sodium-2-(trans-2-carboxymethylvinyl)penem-3-carboxylate.

* * * * *